United States Patent
Guzzo et al.

(10) Patent No.: US 7,064,108 B2
(45) Date of Patent: Jun. 20, 2006

(54) TOPICAL IVERMECTIN COMPOSITION

(75) Inventors: Cynthia A. Guzzo, Rydal, PA (US); Coleen M. Clineschmidt, Perkiomenville, PA (US); George Schorn, North Wales, PA (US); James M. Reynolds, Harleysville, PA (US)

(73) Assignees: Merck & Co., Inc., Rahway, NJ (US); McNeil-PPC, Inc., Fort Washington, PA (US)

( * ) Notice: Subject to any disclaimer, the term of this patent is extended or adjusted under 35 U.S.C. 154(b) by 0 days.

(21) Appl. No.: 10/504,262

(22) PCT Filed: Feb. 4, 2003

(86) PCT No.: PCT/US03/03438

§ 371 (c)(1),
(2), (4) Date: Aug. 9, 2004

(87) PCT Pub. No.: WO03/066009

PCT Pub. Date: Aug. 14, 2003

(65) Prior Publication Data

US 2005/0143325 A1   Jun. 30, 2005

Related U.S. Application Data

(60) Provisional application No. 60/355,082, filed on Feb. 8, 2002.

(51) Int. Cl.
*A01N 43/04* (2006.01)
*A61K 31/70* (2006.01)

(52) U.S. Cl. .......................................... 514/27; 514/30
(58) Field of Classification Search .................. 514/27, 514/30
See application file for complete search history.

(56) References Cited

U.S. PATENT DOCUMENTS

| 4,199,569 | A |   | 4/1980 | Chabala et al. |   |
|---|---|---|---|---|---|
| 5,211,941 | A |   | 5/1993 | Komori et al. |   |
| 5,773,422 | A | * | 6/1998 | Komer | 514/30 |
| 5,858,383 | A |   | 1/1999 | Precopio et al. |   |
| 6,013,636 | A | * | 1/2000 | Harvey | 514/30 |
| 6,103,248 | A | * | 8/2000 | Burkhart et al. | 424/401 |
| 6,262,031 | B1 | * | 7/2001 | Larouche et al. | 514/30 |
| 6,426,333 | B1 | * | 7/2002 | Huet et al. | 514/30 |

OTHER PUBLICATIONS

Youssef et al. Am. J. Trop. Med. Hyg. (1995), vol. 53, pp. 652–653.*

* cited by examiner

*Primary Examiner*—Patrick Lewis
(74) *Attorney, Agent, or Firm*—Richard S. Parr; Valerie J. Camara

(57) ABSTRACT

A topical gel composition comprising between about 0.005 and 1.0% ivermectin, between about 30 and 40% of a pharmaceutically acceptable alcohol, between about 30 and 40% of a pharmaceutically acceptable glycol, and a pharmaceutically acceptable carrier, useful for treating Pediculosis capitis infestation in a human patient.

7 Claims, No Drawings

TOPICAL IVERMECTIN COMPOSITION

CROSS REFERENCE TO RELATED APPLICATION

This application is the National Stage of International Application No. PCT/US03/03438, filed 04 Feb. 2003, which claims the benefit under 35 U.S.C. 119(e) of U.S. Provisional Application No. 60/355,082, filed 08 Feb. 2002.

BACKGROUND OF THE INVENTION

Ivermectin is a semisynthetic, anthelmintic agent derived from the avermectins, a class of highly active broad-spectrum anti-parasitic agents isolated from the fermentation products of *Streptomyces avermitilis*. Ivermectin is a mixture containing at least 90% 5-O-demethyl-22,23-dihydroavermectin $A_{1a}$ and less than 10% 5-O-demethyl-25-de (1-methylpropyl)-22,23-dihyro-25-(1-methylethyl) avermectin $A_{1a}$, generally referred to as 22,23-dihydroavermectin $B_{1a}$ and $B_{1b}$, or $H_2B_{1a}$ and $H_2B_{1b}$, respectively. Ivermectin is described in U.S. Pat. No. 4,199,569. The structural formulas are:

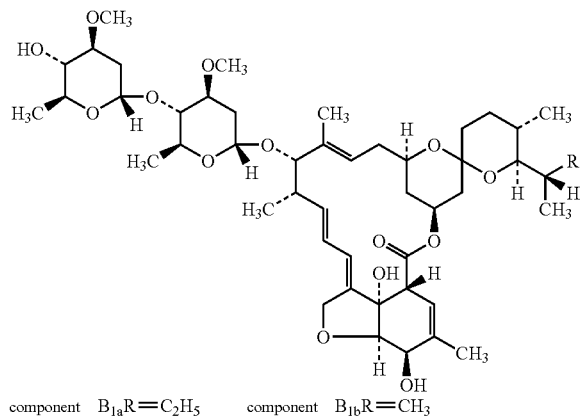

component $B_{1a} R = C_2H_5$    component $B_{1b} R = CH_3$

The compound selectively binds with high affinity to glutamate-gated chloride ion channels which occur in invertebrate nerve and muscle cells, leading to an increase in the permeability of the cell membrane to chloride ions with hyperpolarization of the nerve or muscle cell, resulting in paralysis and death of the parasite. The selectivity of the compound is attributable to the facts that some mammals do not have glutamate gated chloride channels and that the compound has a low affinity for mammalian ligand-gated chloride channels. Ivermectin does not readily cross the blood brain barrier in humans.

Ivermectin is active against various life-cycle stages of many but not all nematodes. It is active against the tissue microfilariae of *Onchocerca volvulus* but not against the adult form. Its activity against *Strongyloides stercoralis* is limited to the intestinal stages.

Ivermectin is commercially available as STROMECTOL® for eradication of *Strongyloides stercoralis*, which causes strongyloidiasis, and *Onchocerca volvulus*, which causes onchocerciasis. Ivermectin is also available as MECTIZAN® for eradication of *Onchocerca volvulus* and *Wuchereria bancrofti*. Ivermectin has a plasma half-life of about 15–20 hours. Its metabolite has a plasma half life of about 3 days.

The recommended dosage for treating strongyloidiasis is a single oral dose designed to provide approximately 200 ug of ivermectin per kg of body weight. Additional doses are generally not necessary in order to eradicate infection.

The recommended dosage for treating onchocerciasis is a single oral dose designed to provide approximately 150 ug of ivermectin per kg of body weight. The most commonly used dose intervals in mass distribution campaigns is 12 months. However, retreatment of individuals may be considered at intervals as short as 3 months. Clinical trials have demonstrated efficacy and tolerability that effectively reduces the dermal microfilarial density to near zero after one month and to successfully maintain a low microfilarial level for up to 12 months.

Ivermectin is also used to treat microfilaremia in patients with lymphatic filariasis caused by *Wuchereria bancrofti*. Ivermectin has not been shown to have any activity against adult worm of any species of *Filarioidea* causing lymphatic filariasis, in tropical pulmonary eosinophilia syndrome, or in lymphadenitis or lymphangitis associated with lymphatic filariasis. Ivermectin is recommended for use in treating microfilaremia in lymphatic filariasis in patients for whom there may be an increased risk of adverse experiences with the use of other microfilaricides, such as in populations of patients who are, or are likely to be co-infected with *Onchocerca volvulus*. The recommended dosage for mass distribution for the treatment of microfilaremic in lymphatia filariasis is a single oral dose of approximately 150 to 200 ug/kg once every 6 months. In endemic areas where treatment can only be administered once every 12 months, a dose of approximately 300 to 400 ug/kg is recommended. These doses are based on studies conducted in patients in Africa, Asia, South America and the Caribbean. Ivermectin was compared with diethylcarbamazine in some of these studies. Overall incidences of adverse experiences for an amicrofilaremic population in mass treatment programs were 1%. The following is a list of the more common adverse experiences reported in studies of microfilaremic patients in the literature: fever, headache, myalgia, asthenia/weakness, cough, anorexia, chills, lethargy, arthralgia, nausea, diaphoresis, sore throat, abdominal pain, light-headedness, malaise epigastric pain, postural hypotension, lung function alterations, dizziness, body pain, gastralgia, chest pain, fatigue, respiratory adverse experiences, testicular tenderness, and ascaris expulsion/elimination of worms. The frequency and intensity of adverse experiences are probably related to the pretreatment microfilarial density. Laboratory abnormalities included eosinophilia, liver function abnormalities and hematuria.

Ivermectin has been used to treat head lice (*Pediculosis capitis*). Glaziou et al. Trop. Med. Parasitol. 45 (1994) 253–254 describe a study in which 26 patients each received a single oral 200 ug/kg dose. The results showed an effectiveness of ivermectin 200 μg/kg single dose against head lice. The authors suggested a second dose on the tenth day to prevent reinfestation from others in the population with head lice. The second dose was not suggested as part of the treatment regimen for the initial infestation.

Youssef et al. Amer. J. Trop. Med. Hyg. 53(6) 1995 pp. 652–653 describe a method of topical application of ivermectin to treat head lice. Ivermectin was found to have an absolute curative effect after a single topical application.

Dunne et al. Trans. R. Soc. Trop. Med. Hyg. 85: 550–551 describe a study in which a single oral dose of 100–200 ug/kg of ivermectin was administered to patients with head lice. They reported a significant, but not absolute, effect on head lice infestation.

U.S. Pat. No. 6,262,031 describes a method for treating head lice infestation by orally administering to the patient, over a period of time of about one week, a total amount of ivermectin of between about 400 ug/kg and 1200 ug/kg.

SUMMARY OF THE INVENTION

The invention is a topical gel composition comprising an amount between about 0.005 and 1.0 % ivermectin, between about 30 and 40% of a pharmaceutically acceptable alcohol, between about 30 and 40% of a pharmaceutically acceptable glycol, and a pharmaceutically acceptable carrier.

In a class of the compositions of the invention, the pharmaceutically acceptable glycol is propylene glycol and the pharmaceutically acceptable alcohol is ethyl alcohol.

In a subclass of the class of compositions, the compositions additionally comprise between about 4 and 8% of a pharmaceutically acceptable nonionic surfactant, between about 1 and 2.5% d-limonene, and between about 0.1 and 1% of a pharmaceutically acceptable viscosifying agent.

In a group of the subclass of compositions, the pharmaceutically acceptable viscosifying agent is hydroxypropylcellulose.

In a subgroup of the group, of compositions, the amount of ivermectin is between about 0.007 and 0.013%.

In a family of the subgroup of compositions, the compositions include about 0.009 to 0.011 ivermectin, about 32 to 34% propylene glycol, about 32 to 34% ethyl alcohol, about 5 to 7% sorbitan mono-9-octadecenoate poly(oxy-1,2-ethanediyl derivative, about 1.7 to 1.8% d-limonene, about 0.4 to 0.6% hydroxypropylcellulose, and a pharmaceutically acceptable carrier.

The invention is also a method for treating Pediculosis capitis infestation in a human patient which comprises topically administering to the human a composition described above on one day.

The invention also includes a topical composition comprising between about 0.005 and 0.1% ivermectin, and a pharmaceutically acceptable carrier, and a method for treating Pediculosis capitis infestation in a human patient which comprises topically administering this composition to the human. The topical composition is formulated in a conbventional manner using pharmaceutically acceptable excipients such as water and viscosifying agents to achieve desirable formulation characteristics.

Formulation component amounts referenced above and below are on a weight/volume basis. Thus, a formulation having 1% ivermectin contains 1 gram of ivermectin per 100 ml of total composition.

DETAILED DESCRIPTION OF THE INVENTION

The composition of the present invention provides a means for topically delivering ivermectin to a patient over a long residence time that allows the active agent to disable the head lice. This is particularly important since ivermectin is a slow acting drug. By providing a long residence time, the cosmetically acceptable formulation allows for therapeutically effective use of environmentally acceptable low quantities of ivermectin. Additionally, use of low quantities of ivermectin reduces human systemic absorption of the active ingredient.

Pharmaceutically Acceptable Alcohol

Pharmaceutically acceptable alcohols useful in the present invention include methanol, benzyl alcohol, ethyl alcohol and isopropyl alcohol. Ethyl alcohol is the preferred alcohol.

Pharmaceutically Acceptable Glycols

Pharmaceutically acceptable glycols are non-toxic, and do not irritate the skin at the concentrations used in compositions of the present invention. Suitable glycols include, but are not limited to, propylene glycol such as propylene glycol 200 (PEG 200), 1,3-butylene glycol, polyethylene glycol 400 (PEG 400), methylpropanediol, ethoxydiglycol (e.g. Transcutol®), hexylene glycol, and dipropylene glycol. Propylene glycol is preferred.

D-limonene

D-limonene, available from National Products, is a terpenoid (d-1-methyl-4-(1-methylethenyl)cyclohexene (Kugker, Kovats Helv. Chim. Acta 46, 1480 (1963) and J. L. Simonsen, The Terpenes vol. I (University Press, Cambridge, $2^{nd}$ ed., 1947) pp. 143–165 , constitutes about 90 percent of crude citrus oil, and is purified from the oil by steam distillation. D-limonene has some pediculicidal and ovicidal activity. D-limonene is thought to cause an increase in the spontaneous activity of sensory nerves. The heightened activity sends spurious information to motor nerves and results in twitching, lack of coordination, and convulsions. The central nervous system may also be affected, resulting in additional stimulation of motor nerves. Massive over stimulation of motor nerves leads to rapid knockdown paralysis. However, adult fleas and other insects may recover from knockdown. Crude citrus peel oils and products prepared with crude oils may be more toxic to animals than products containing purified d-limonine or linalool.

Pharmaceutically Acceptable Viscosifying Agent

Pharmaceutically acceptable viscosifying agents suitable for the present invention are those agents which provide viscosity to the topical therapeutic formulation such that formulation can be effectively applied to the infested area, including but not limited to hydroxypropylcellulose (e.g. Klucel H A), carrageenans, microcrystalline cellulose, alginates, gellan gum, xanthan gum, veegum, hydroxyethylcellulose, guar gum and carbomers. Hydroxypropylcellulose is preferred.

Pharmaceutically Acceptable Nonionic Surfactant

Pharmaceutically acceptable nonionic surfactants are those which are compatible, especially with regard to solubility and chemical stability, with ivermectin. Suitable nonionic surfactants, which decrease surface tension and allow ivermectin to penetrate the lice eggs, include, but are not limited to, sorbitan mono-9-octadecenoate poly(oxy-1,2-ethanediyl derivatives such as polyoxyethylene (20) sorbitan mono-oleate, sorethytan (20) mono-oleate, polyethylene oxide sorbitan mono-oleate, and sorbitan mono-oleate polyoxyethylene (Polysorbate 80) and polyoxyethylene-10-oleyl-ether (Brij 97). Polysorbate 80 is a nonionic surfactant used widely as an additive in foods, pharmaceutical preparations, and cosmetics as an emulsifier, dispersant, or stabilizer.

In a composition of the present invention, the pharmaceutically acceptable carrier is a solvent suitable for preparing stable gel compositions for topically administering therapeutically effective amounts of ivermectin, for example, water. If the carrier is water, amounts are preferably between 15 and 35%. Amounts of water less than 15% introduce problematic systemic absorption of ivermectin, while amounts of water greater than 35% lead to ivermectin chemical instability.

Other materials that may be suitable include antioxidants such as BHA, BHT, glycerine and its derivatives, parabens, vanillins, sorbic acid, sodium benzoate, benzoic acid, imidazoline and citric acid.

The gels of the present invention are semisolid systems consisting of either suspensions made up of small inorganic particles or large organic molecules interpenetrated by a liquid. Gels suitable for the present invention are aqueous gels of organic polymers. Single-phase gels consist of organic macromolecules uniformly distributed throughout a liquid in such a manner that no apparent boundaries exist between the dispersed macromolecules and the liquid.

Dosage

The gel compositions are topically applied to the patient in an amount of between about 10 ml and 90 ml, in one dose administration or multiple separate dose administration, e.g. 2, 3 or 4 administrations. If administered in multiple separate dosage, each separate dose is between about 10 ml and 90 ml. Thus, in a treatment involving a gel composition having 0.005% of ivermectin (0.005 g/100 ml), administration of 10 ml of the composition delivers 0.5 mg of ivermectin. In a treatment involving a gel composition having 1% ivermectin (1 g/100 ml), administration of 90 ml of the composition delivers 900 mg of ivermectin. The compositions of the invention are therefore suitable for delivery of as little as 0.5 mg of ivermectin in a single application and as much as 900 mg of ivermectin in a single application. The option of multiple separate dosing provides an opportunity to administer greater total quantities of ivermectin to the patient The method of the invention involves multiple dosing of ivermectin in order to eradicate head lice infestation. According to the method, the first dose is administered after identification of infestation, evidenced by the presence of live lice and eggs (nits) on the patient. The first dose kills lice and eggs present at the time of dosing. Subsequent dosing kills lice that subsequently hatch following the first dose, in addition to lice and eggs that may have survived initial dosing. Doses are administered to the patient by applying the topical composition to the patient in quantities sufficient to saturate the scalp The invention is intended to be allowed to dry on the hair so that the hair may be styled as usual.

After an application time of up to several hours, the invention may be followed by shampoo hair cleanings with shampoos typically used for cleaning hair such as PRELL® shampoo (e.g., those which clean hair but which do not contain active ingredients known to be useful for killing head lice, such as permethrin, lindane, pyrethrin, carbaryl, and malathion).

It is also contemplated that the method of the present invention is useful for preventing head lice infestation in a human susceptible to such infestation, e.g. a human coming into close contact with an infected individual.

Therapeutic Use

Therapeutic application of the compositions of the invention involves applying the topical preparation to dry scalp hair infested with head lice. The composition is maintained on the scalp hair at least 10 minutes to allow time for the insecticide to kill the adult lice and lice eggs. Preferably, the topical preparation is left on the scalp hair at least about one hour, and more preferably at least about 3–4 hours. In a particularly preferred therapy, the topical preparation is left on the scalp hair overnight.

The amount of composition applied is that amount sufficient to saturate the scalp. Preferably, at least about 40 ml of topical preparation is applied to totally saturate the roots of the hair taking care to cover the entire scalp. This procedure will reduce the problem with current commercial compositions in which people are not sufficiently saturating their hair with insecticide.

Preferably, a second application of the topical preparation is done about about one week after the first application. The second application will kill any eggs laid by adults that survived the initial application, will kill any nymphs that hatched following the initial application, increases the ovicidal kill and reduces the potential for reinfestation. The second application of the topical preparation will prevent reinfestation by nymphs. A third application may be applied one week after the second application if desired.

The method of the present invention is also useful in topical combination with other known head lice treatments, including, but not limited to, treatments with permethrin (NIX®, ELIMITE®), lindane (KWELL®, SCABENE®), pyrethrin (including A200 shampoo, Clear Total Lice Elimination System, and Maximum Strength Rid Lice Killing Shampoo), carbaryl, malathion, formic acid rinses, combing, including thermal combing, and shampooing, including shampooing with enzymes that dissolve chitinous cement on nits. It is also contemplated that oral forms of moxidectin, the active ingredient in QUEST™ Gel, as well as oral forms of doramectin and ivermectin (as described in U.S. Pat. No. 6,262,031), would be suitable for treating head lice infestation by dosing in accordance with treatment regimens described herein. It is also contemplated that abamectin (U.S. Pat. No. 4,310,519) (5-O-demethylavermectin $A_{1a}$ and 5-O-demethyl-25-de(1-methylpropyl)-25-(1-methylethyl) avermectin $A_{1a}$ (4:1)) may be used to treat head lice infestation in accordance with the procedures described in the subject application.

Coadministration of both oral and topical formulations of ivermectin includes simultaneous or concomitant administration (defined as occurring on the same day) as well as combination administrations to the patient over a period of up to about 10 days. Thus, in one exemplary coadministration, the oral ivermectin formulation and the topical ivermectin formulation are administered to the patient on the same day. In another exemplary coadministration, the oral ivermectin formulation is administered on the first treatment day and the topical ivermectin formulation is administered on the second treatment day, which may be, for example, 7 days after the first day. In another exemplary coadministration, the topical ivermectin formulation is administered on the first treatment day and the oral ivermectin formulation is administered on the second treatment day, which may be, for example, 7 days after the first day.

The carrier can also include a wide variety of optional ingredients. A preferred optional ingredient is an attractant for the head lice, such as ammonia. An attractant may be helpful because lice tend to flee the scalp before the scalp hair can be totally saturated with the topical preparation, especially the small nymph stages of the lice. The attractant would thus reduce the chance of later reinfestation or fomite transmission of any louse that might try to flee during application of the topical preparation.

Additional active ingredients effective for killing head lice may be used in the formulations of the present invention, or administered with the formulations of the present invention. The killing agent admixed in the carrier includes any material effective in killing the head lice such as an insecticide. The following insecticides, as well as others not listed, are suitable for use in the topical preparation in combination with ivermectin: gamma benzene hexachloride, malathion, permethrin, pyrethrin, piperonyl butoxide, moxidectin, other macrocyclic lactones such as compound F28249, doramectin, pyrantel pamoate, fenbendaxole, oxibendazole, benzimidazole, thiabendazole, abamectin, avermectin, carboxyl, DDT (chlorophenothene), cromiton, benzyl benzoate, temephos, coumaphos, diazinon, sumithrine, fluorescein, pyrantel embonate, carbophenothion, chlorfenvinphos, crotoxyphos, fenitrothion, derris, bromocyclen, diflubenzuron, organophosphates, organochlorines, hexachlorocyclohexanes, crotoxyphos (plus dichlorvos), stirofos, tetrachlorvinphos, dioxathion, phosmet, bromocyclen, famphur, fenthion, methoxychlor, toxophene, trichlorfon, cypermethrin, bioallethrin, cyano substituted pyrethroid, phenothrin, pirimiphos methyl, carbaryl, propoxur, temephos, nicotine, pralidoxine, parathion, and natural oils such as coconut oil, anise, ylang ylang, garlic and lavender. Preferably, the insecticide is lipophilic so that it can more readily pass through the lipophilic membranes surrounding the louse larva in the egg. Some examples of preferred killing agents are botanical agents (e.g., pyrethrin, anise, ylang ylang), synthetic derivatives of botanical agents (e.g., permethrin), and chemical insecticides (e.g., organochorines, organophosporates, carbamates, anti-cholinesterases). It is preferred to use insecticides that are allowed on formulary by the FDA. The amount of insecticide in the topical preparation is usually within a range of from about 0.5% to about 10% insecticide of the topical preparation. The insecticide can usually be simply mixed into the topical preparation.

Preparation

Preparation of the gel formulations of the invention involve the sequential mixing of the pharmaceutically acceptable alcohol in water, the pharmaceutically acceptable glycol, and the active ingredient, ivermectin. Additional desirable ingredients such as d-limonene, viscosifying agent and nonionic surfactant may be added with the active ingredient.

A preferred preparation involves the sequential mixing of ethyl alcohol in water, propylene glycol, and the active ingredient, ivermectin. Additional desirable ingredients such as d-limonene, hydroxypropylcellulose, and a sorbitan mono-9-octadecenoate poly(oxy-1,2-ethanediyl derivative, may be added with the active ingredient.

EXAMPLE 1

Using the general procedure described above, the following formulations were prepared with ivermectin, ethyl alcohol, propylene glycol and water.

|  | 1a | 1b | 1c |
| --- | --- | --- | --- |
| Ivermectin | 0.01 g | 0.01 g | 0.01 g |
| Ethyl alcohol | 30 g | 33 g | 40 g |
| Propylene glycol | 40 g | 33 g | 30 g |
| Water | q.s. 100 ml | q.s. 100 ml | q.s. 100 ml | q.s. means quantities sufficient to reach 100 ml.

EXAMPLE 2

Using the general procedure described above, the following formulations were prepared with ivermectin, ethyl alcohol, propylene glycol, Polysorbate 80, d-limonene, hydroxypropylcellulose and water.

|  | 2a | 2b | 2c |
| --- | --- | --- | --- |
| Ivermectin | 0.01 g | 0.01 g | 0.01 g |
| Ethyl alcohol | 30 g | 33 g | 40 g |
| Propylene glycol | 40 g | 33 g | 30 g |
| Polysorbate 80 | 4 g | 6 g | 8 g |
| D-limonene | 1 g | 2 g | 2.5 g |
| Hydroxypropylcellulose | 0.1 g | 0.5 g | 2.5 g |
| Water | q.s. 100 ml | q.s. 100 ml | q.s. 100 ml | q.s. means quantities sufficient to reach 100 ml.

EXAMPLE 3

Patients infested with head lice are treated with two 25 ml topical applications of the composition 2b described in Example 2 over a period of 8 days. The composition is applied to the patient's scalp using a technique resulting in complete coverage of the scalp. After the composition is administered, the composition is allowed to remain on the patient for 1 hour and then removed via shampooing.

EXAMPLE 4

The treatment procedure described in Example 3 is repeated except that the composition is allowed to remain on the patient overnight and then removed via shampooing.

EXAMPLE 5

Patients infested with head lice are treated with three 20 ml topical applications of the composition 2b described in Example 2 over a period of 8 days. The composition is applied to the patient's scalp using a technique resulting in complete coverage of the scalp. After the composition is administered, the composition is allowed to remain on the patient for 1 hour and then removed via shampooing.

EXAMPLE 6

The treatment procedure described in Example 5 is repeated except that the composition is allowed to remain on the patient overnight and then removed via shampooing.

EXAMPLE 7

The procedure of Example 3 was repeated with the additional step of administering permethrin according to procedures for administering permethrin which are described in the Physician's Desk Reference, 52$^{nd}$ Edition (1998), page 9280.

EXAMPLE 8

Patients infested with head lice are treated with 1) on treatment day 1, the number of oral tablets containing 3 mg of ivermectin sufficient to deliver 200 μg of ivermectin per kg of patient weight, and 2) on treatment day 8 (seven days after the first treatment day), a 25 ml topical application of the composition 2b described in Example 2. The topical composition is applied to the patient's scalp using a technique resulting in complete coverage of the scalp. After the topical composition is administered, the composition is allowed to remain on the patient for 1 hour and then removed via shampooing.

What is claimed is:

1. A topical gel composition comprising between about 0.005 and 1.0% ivermectin, between about 30 and 40% of a pharmaceutically acceptable alcohol, between about 30 and 40% of a pharmaceutically acceptable glycol, and a pharmaceutically acceptable carrier.

2. A composition of claim 1 wherein the pharmaceutically acceptable glycol is propylene glycol and the pharmaceutically acceptable alcohol is ethyl alcohol.

3. A composition of claim 2 which additionally comprises between 4 and 8% of a pharmaceutically acceptable non-ionic surfactant, between about 1 and 2.5% d-limonene, and between about 0.1 and 1% of a pharmaceutically acceptable viscosifying agent.

4. A composition of claim 3 wherein the viscosifying agent is hydroxypropylcellulose.

5. A composition of claim 4 comprising about 0.009 to 0.011% ivermectin, about 32 to 34% propylene glycol, about 32 to 34% ethyl alcohol, about 5 to 7% sorbitan mono-9-octadecenoate poly(oxy-1,2-ethanediyl derivative, about 1.7 to 1.8% d-limonene, about 0.4 to 0.6% hydroxypropylcellulose, and a pharmaceutically acceptable carrier.

6. A method for treating Pediculosis capitis infestation in a human patient which comprises topically administering to the human a composition of claim 1.

7. A method for treating Pediculosis capitis infestation in a human patient which comprises topically administering to the human a composition of claim 1 on one day and orally administering an oral composition comprising ivermectin on a second day.

* * * * *